US008610769B2

(12) United States Patent
Buxton et al.

(10) Patent No.: US 8,610,769 B2
(45) Date of Patent: Dec. 17, 2013

(54) MEDICAL MONITOR DATA COLLECTION SYSTEM AND METHOD

(75) Inventors: Kip Buxton, Arvada, CO (US); David Orian, Tracy, CA (US); Robert Rawlins, Westminster, CO (US); Tom Wilmering, Westminster, CO (US)

(73) Assignee: Covidien LP, Mansfield, MA (US)

( * ) Notice: Subject to any disclaimer, the term of this patent is extended or adjusted under 35 U.S.C. 154(b) by 349 days.

(21) Appl. No.: 13/036,472

(22) Filed: Feb. 28, 2011

(65) Prior Publication Data

US 2012/0218404 A1   Aug. 30, 2012

(51) Int. Cl.
*G09B 9/00* (2006.01)
*G06K 9/00* (2006.01)
*A61B 5/00* (2006.01)
*H04N 1/04* (2006.01)

(52) U.S. Cl.
USPC ........... 348/121; 382/128; 382/100; 600/323; 358/474

(58) Field of Classification Search
USPC .......................................... 348/121; 358/474
See application file for complete search history.

(56) References Cited

U.S. PATENT DOCUMENTS

| | | |
|---|---|---|
| 3,638,640 A | 2/1972 | Shaw |
| 4,936,679 A | 6/1990 | Mersch |
| 4,971,062 A | 11/1990 | Hasebe et al. |
| 4,974,591 A | 12/1990 | Awazu et al. |
| 5,028,787 A | 7/1991 | Rosenthal et al. |
| 5,065,749 A | 11/1991 | Hasebe et al. |
| 5,084,327 A | 1/1992 | Stengel |
| 5,275,159 A | 1/1994 | Griebel |
| 5,348,005 A | 9/1994 | Merrick et al. |
| 5,483,646 A | 1/1996 | Uchikoga |
| 5,730,124 A | 3/1998 | Yamauchi |
| 5,779,631 A | 7/1998 | Chance |
| 5,783,821 A | 7/1998 | Costello, Jr. |
| 5,830,139 A | 11/1998 | Abreu |
| 5,831,598 A | 11/1998 | Kauffert et al. |
| 5,871,442 A | 2/1999 | Madarasz et al. |
| 5,873,821 A | 2/1999 | Chance et al. |
| 6,081,742 A | 6/2000 | Amano et al. |
| 6,120,460 A | 9/2000 | Abreu |
| 6,134,460 A | 10/2000 | Chance |
| 6,285,895 B1 | 9/2001 | Ristolainen et al. |
| 6,312,393 B1 | 11/2001 | Abreu |

(Continued)

FOREIGN PATENT DOCUMENTS

| | | |
|---|---|---|
| DE | 69123448 | 5/1997 |
| EP | 0615723 | 9/1994 |

(Continued)

OTHER PUBLICATIONS

Buschman, J.P., et al.; "Principles and Problems of Calibration of Fetal Oximeters," Biomedizinische Technik, vol. 42, pp. 265-266 (1997).

(Continued)

*Primary Examiner* — Joseph Ustaris
*Assistant Examiner* — Rebecca Volentine

(57) ABSTRACT

A system and method for generating results indicative of physiological parameters of a patient and for capturing the results. The capture of the results may include recordation of the results through the use of a camera, while the physiological parameters may be generated through monitoring of a patient or by simulating such monitoring.

20 Claims, 5 Drawing Sheets

(56) References Cited

U.S. PATENT DOCUMENTS

| | | | |
|---|---|---|---|
| 6,353,750 B1 | 3/2002 | Kimura et al. | |
| 6,397,091 B2 | 5/2002 | Diab et al. | |
| 6,415,236 B2 | 7/2002 | Kobayashi et al. | |
| 6,419,671 B1 | 7/2002 | Lemberg | |
| 6,461,305 B1 | 10/2002 | Schnall | |
| 6,487,439 B1 | 11/2002 | Skladnev et al. | |
| 6,544,193 B2 | 4/2003 | Abreu | |
| 6,549,795 B1 | 4/2003 | Chance | |
| 6,591,122 B2 | 7/2003 | Schmitt | |
| 6,606,509 B2 | 8/2003 | Schmitt | |
| 6,618,042 B1 | 9/2003 | Powell | |
| 6,622,095 B2 | 9/2003 | Kobayashi et al. | |
| 6,628,975 B1 | 9/2003 | Fein et al. | |
| 6,662,030 B2 | 12/2003 | Khalil et al. | |
| 6,675,029 B2 | 1/2004 | Monfre et al. | |
| 6,687,519 B2 | 2/2004 | Steuer et al. | |
| 6,690,958 B1 | 2/2004 | Walker et al. | |
| 6,714,245 B1 | 3/2004 | Ono | |
| 6,731,274 B2 | 5/2004 | Powell | |
| 6,785,568 B2 | 8/2004 | Chance | |
| 6,793,654 B2 | 9/2004 | Lemberg | |
| 6,850,053 B2 | 2/2005 | Daalmans et al. | |
| 6,850,788 B2 * | 2/2005 | Al-Ali | 600/323 |
| 6,898,451 B2 | 5/2005 | Wuori | |
| 6,949,081 B1 | 9/2005 | Chance | |
| 7,035,697 B1 | 4/2006 | Brown | |
| 7,041,063 B2 | 5/2006 | Abreu | |
| 7,043,289 B2 | 5/2006 | Fine et al. | |
| 7,065,392 B2 | 6/2006 | Kato | |
| 7,095,491 B2 | 8/2006 | Forstner et al. | |
| RE39,268 E | 9/2006 | Merrick et al. | |
| 7,236,811 B2 | 6/2007 | Schmitt | |
| 7,239,902 B2 | 7/2007 | Schmitt et al. | |
| 7,272,426 B2 | 9/2007 | Schmid | |
| 7,428,432 B2 | 9/2008 | Ali et al. | |
| 7,469,158 B2 | 12/2008 | Iyer et al. | |
| 7,551,950 B2 | 6/2009 | Cheng | |
| 7,621,877 B2 | 11/2009 | Schnall | |
| 2002/0042558 A1 | 4/2002 | Mendelson | |
| 2002/0156354 A1 | 10/2002 | Larson | |
| 2002/0198443 A1 | 12/2002 | Ting | |
| 2003/0023140 A1 | 1/2003 | Chance | |
| 2003/0195402 A1 | 10/2003 | Fein et al. | |
| 2004/0171920 A1 | 9/2004 | Mannheimer et al. | |
| 2005/0113651 A1 | 5/2005 | Wood et al. | |
| 2005/0113656 A1 | 5/2005 | Chance | |
| 2005/0192488 A1 | 9/2005 | Bryenton et al. | |
| 2005/0228248 A1 | 10/2005 | Dietiker | |
| 2006/0020181 A1 | 1/2006 | Schmitt | |
| 2006/0247501 A1 | 11/2006 | Ali | |
| 2008/0081969 A1 | 4/2008 | Feldman et al. | |
| 2008/0221462 A1 | 9/2008 | Baker | |
| 2009/0174805 A1 * | 7/2009 | Alberth et al. | 348/345 |
| 2009/0204683 A1 * | 8/2009 | Tipirneni | 709/217 |
| 2009/0221880 A1 * | 9/2009 | Soderberg et al. | 600/300 |
| 2011/0064283 A1 * | 3/2011 | Hodson et al. | 382/128 |
| 2011/0242617 A1 * | 10/2011 | King et al. | 358/474 |
| 2012/0020532 A1 * | 1/2012 | Snow et al. | 382/112 |

FOREIGN PATENT DOCUMENTS

| | | |
|---|---|---|
| JP | 63275325 | 11/1988 |
| JP | 2237544 | 9/1990 |
| JP | 3124073 | 5/1991 |
| JP | 5049624 | 3/1993 |
| JP | 2005034472 | 2/2005 |
| WO | WO9316629 | 9/1993 |
| WO | WO9639927 | 12/1996 |
| WO | WO0021438 | 4/2000 |
| WO | WO0140776 | 6/2001 |
| WO | WO0176471 | 10/2001 |
| WO | WO03039326 | 5/2003 |
| WO | WO2008035076 | 3/2008 |
| WO | WO0176461 | 10/2011 |

OTHER PUBLICATIONS

Earthrowl-Gould, T., et al.; "Chest and abdominal surface motion measurement for continuous monitoring of respiratory function," Proc. Instn Mech Engrs, V215, Part H; pp. 515-520 (2001).

A. Johansson; "Neural network for photoplethysmographic respiratory rate monitoring," Medical & Biological Engineering & Computing, vol. 41, pp. 242-248 (2003).

Johnston, W.S., et al.; "Extracting Breathing Rate Information from a Wearable Reflectance Pulse Oximeter Sensor," Proceedings of the 26th Annual International conference of the IEEE EMBS, San Francisco, California; Sep. 1-5, 2004; pp. 5388-5391.

Spigulis, Janis, et al.; "Optical multi-channel sensing of skin blood pulsations," Optical Sensing, Proceedings of SPIE, vol. 5459, pp. 46-53 (2004).

* cited by examiner

MEDICAL MONITOR DATA COLLECTION SYSTEM AND METHOD

BACKGROUND

The present disclosure relates generally to medical devices and, more particularly, to visual detection of displayed information thereon.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

To insure that pulse oximeters are operating properly, testing methodologies may be implemented. These methodologies may include tests designed to transmit various known inputs to the pulse oximeter. Expected results corresponding to each of the known inputs may be compared to the actual results generated by the pulse oximeter to determine if the pulse oximeter is properly operating. However, directly obtaining the actual results of the testing procedures via physical contact with elements of the pulse oximeter may lead to corruption of the actual values to be measured. Accordingly, there is a need to receive physiological values from pulse oximetry systems without impacting the actual values calculated by the pulse oximetry system. Additionally, it would be beneficial to be able to monitor and log the operation of a medical device while being used to monitor a patient.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Physiological monitors may receive data signals, calculate physiological parameters of a patient based on the data signal, and display the results of this calculation. To insure that these physiological monitors are functioning properly, simulated signals may be transmitted to the physiological monitor in place of actual signals derived from a patient. These simulated signals may be generated to test specific performance characteristics of the physiological monitor. For example, the simulated signals may be of a type to generate an alarm in the physiological monitor. Moreover, a range of simulated signals may be transmitted to the physiological monitor to test a wide variety of signals that the monitor may be asked to receive and to calculate results based thereon. The results of this simulation process may be collected and reviewed to insure proper operation by the monitor. However, as direct collection via physical interface with the monitor may interfere with the results generated by the monitor, a non-physical collection method including capturing images of the physiological monitor as a simulation is proposed. That is, a camera may be utilized to capture still or video images of the monitor as the monitor is receiving simulated data signals. These images may then be converted into data (i.e., results) that may be stored in, for example, a computer and displayed, for example, on a display of a computer.

Additionally, capturing of video and/or still images of the operation of a monitor for current or later analysis may be accomplished through the use of the monitor and camera. That is, the monitor may be in use (i.e., connected to a patient) for a period of time while the camera operates to log, for example, any alarms that occur while the patient is being monitored. The camera may also be implemented in conjunction with a monitor to capture events that occur during a prolonged clinical study, such as monitoring patients suffering from sleep apnea, for example, during the course of a sleep study.

Figure 1:
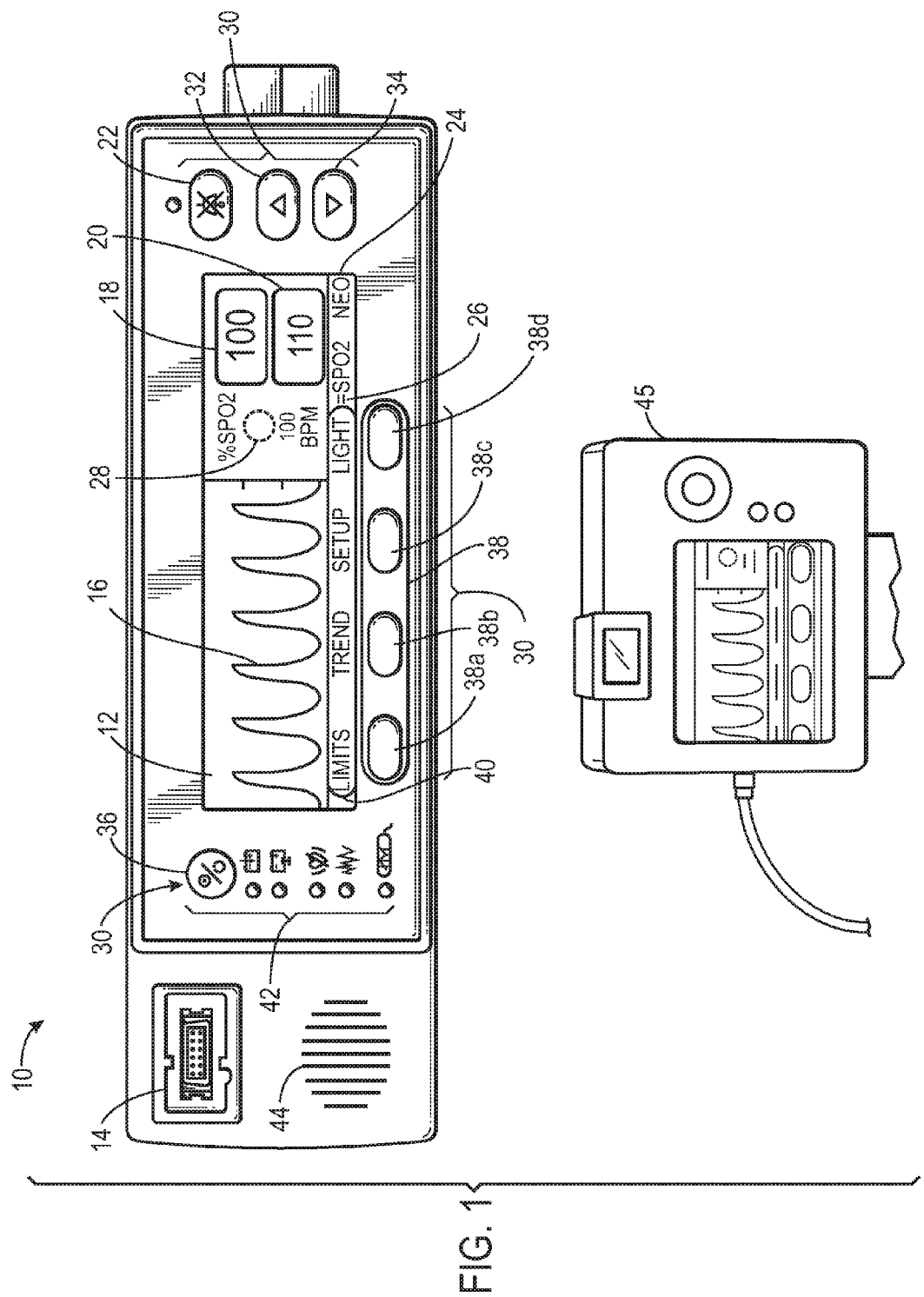
FIG. 1 illustrates a perspective view of a patient monitor, in accordance with an embodiment.

Turning to FIG. 1, a perspective view of a medical device is illustrated in accordance with an embodiment. The medical device may be a patient monitor 10. For example, the monitor 10 may be a pulse oximeter, such as those available from Nellcor Puritan Bennett LLC. As shown, the patient monitor 10 is a pulse oximeter designed to detect and monitor blood oxygen saturation levels, pulse rate, and so forth. The monitor 10 may be, for example, processor-based and software-controlled where the software may be stored in memory, such as RAM, ROM, or flash memory. The monitor 10 may also be configured to display calculated parameters on a display 12, which may be a cathode ray tube or liquid crystal display, for example. Moreover, the display 12 may include an optional touch screen.

In general, the display 12 may show processed physiological data and/or other data received through a medical device interface 14, such as a cable connection port, from, for example, a patient sensor (discussed below) coupled to the cable connection port. In other embodiments, the medical device interface 14 may include any suitable type of interface for connecting to a medical device. For example, in certain embodiments, the medical device interface 14 may include a wireless interface. As noted above, processed data generated from data received at the medical device interface 14 may be displayed on the display 12. The display 12 may be used to display a plethysmographic ("pleth") waveform display 16, an oxygen saturation display 18, and/or a pulse rate display 20. The oxygen saturation display 18 may be a functional arterial hemoglobin oxygen saturation measurement displayed as units of percentage $SpO_2$. The pulse rate display 20 may indicate a patient's pulse rate in beats per minute. The display 12 also may be used to show topic-specific screens related to the physiological data, such as a "blip" display that includes pulse amplitude blips, a real-time trend display, and an alarm limit and monitoring mode display. Moreover, the display 12 may be used to display user interface options, such as a setup and/or configuration screen for adjusting parameters such as alarm volume, display scales, and button sizes and locations, among others.

The display 12 may also include an alarm status indicator (not shown), such as a bell that flashes when an alarm condition is present. When the alarm is silenced using the alarm silence button 22, an alarm silence indicator, such as a slash and a timer, may be shown to indicate that the alarm is temporarily silenced. When the alarm is silenced through an "all mute" menu selection, which is permanent until power is cycled or deselected using menu, an alarm status indicator with a slash may shown to indicate that alarm has been silenced. Further, the display 12 may include mode setting information such as neonatal mode alarm limits or adult mode alarm limits indicators 24 and special settings such as a fast response mode setting indicator 26, which indicates if the patient monitor 10 is operating in a fast alarm response mode rather than a normal alarm mode. In some embodiments, the patient monitor 10 may employ SatSeconds™ by Nellcor™ to detect alarms and manage nuisance alarms. SatSeconds™ may include activation of an alarm based on limits that may include the integral of time and depth of a desaturation event and may include an indicator 28 that may serve to inform the caretaker that a $SpO_2$ reading has been detected outside of the limit settings.

Figure 2:
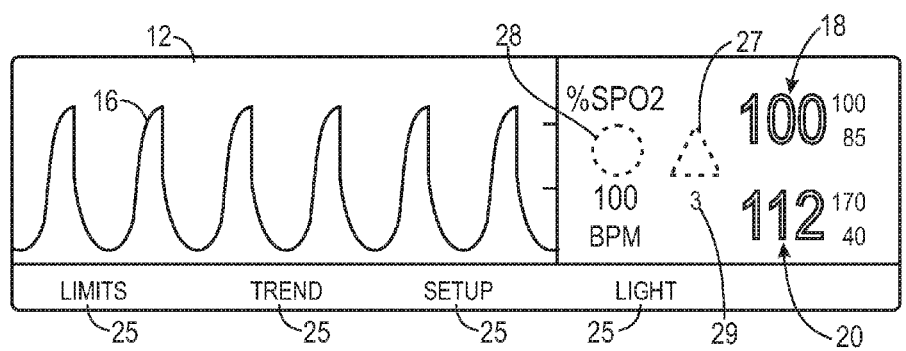
FIG. 2 illustrates a screen shot of a display of the patient monitor of FIG. 1, in accordance with an embodiment.

One embodiment of the display 12 is illustrated in FIG. 2. As illustrated, the screenshot of the display 12 in FIG. 2 includes a pleth waveform display 16, an oxygen saturation display 18, and a pulse rate display 20. Additionally, the display may include a plurality of soft key icons 25 as well as a graphical indicator 27 that may provide information to a user related to the occurrence, frequency, and/or magnitude of the patterns be based on a saturation pattern detection index (SPDi) calculation. The SPDi may be defined as a scoring metric associated with the identification of a saturation trend pattern that has been generated and may correlate to ventilatory instability in a population of sleep lab patients. That is, the SPD calculation may be capable of notifying a user of ventilatory instability that corresponds to a certain SPDi value. In embodiments, when the SPDi is at or above a threshold setting, the user may be notified via the graphical indicator 27.

As illustrated in FIG. 2, the graphical indicator 27 may be represented on display 12 as a dashed triangle that may graphically fill from bottom to top as a monitored and/or calculated value increases. For example, in one embodiment, the graphical indicator 27 may gradually fill as the calculated SPDi increases. Further, the graphical indicator 27 may include a tolerance level indicator 29 that displays an index, for example 1, 2, or 3, for tolerance or sensitivity settings of High, Medium, and Low, respectively, in conjunction with the calculation of the SPDi. The tolerance settings may set the threshold for triggering a change in the graphical indicator 27 and/or for triggering SPD-associated alarms.

Returning to FIG. 1, the monitor 10 may also include selectable inputs 30 that may be used to control operating functions of the patient monitor 10. The selectable inputs 30 may include fixed function keys, such as the alarm silence button 22, up arrow key 32, down arrow key 34, and a power key 36. For example, the arrow keys 32 and 34 may be actuated to adjust alarm limits and/or to vary the physiological information shown on the display 12. Furthermore, the fixed function keys may be programmed to control multiple functions or to operate in different manners based upon various factors, such as the duration the key is pressed, the simultaneous activation of other keys, and so forth. For example, an up arrow key 32 and down arrow key 34 may allow for upwards and downwards scrolling more rapidly based upon how long the respective key is held down.

The monitor 10 may also include programmable function keys ("soft keys") 38, and associated soft key icons 25 in the soft key menu 40. For example, four soft keys 38a, 38b, 38c, and 38d may be pressed to select a corresponding function indicated by the respective soft key icon 25. The soft key icon menu 40 indicates which software menu items can be selected through the soft keys 38. Pressing a soft key 38 associated with, such as below, above, or next to an icon 25, selects the option. For example, the soft key 38a may be pressed to display "LIMITS" information, while the soft key 38b may be pressed to display "TREND" information. In certain embodiments, the soft keys 38 may be programmed to display operating information such as alarm limits, historic trends, setup menus, and alarm volume settings, among others. Moreover, for example, a caretaker may actuate the soft keys 38 to display various operating menus, and then may use the arrow keys 32 and 34 to adjust operating parameters.

In addition to the selectable inputs 30, the monitor 10 may include various indicators 42 (e.g., indicator lights and display screen graphics) that facilitate operation of the monitor 10 and observation of a patient's physiological metrics (e.g., pulse rate). Some of the indicators 42 are specifically provided to facilitate monitoring of a patient's physiological parameters. For example, the indicators 42 may include representations of the most recently measured values for $SpO_2$, pulse rate, and pulse amplitude. Other indicators 42 may be specifically provided to facilitate operation of the monitor 10. For example, the indicators 42 may include an A/C power indicator, a low battery indicator, an alarm silence indicator, a mode indicator, and so forth. The monitor 10 may also include a speaker 44 for emitting audible indications (e.g., alarms) in conjunction with the operation of the monitor 10.

Also illustrated in FIG. 1 is a camera 45. This camera 45 may be, for example, a free standing device such as a digital camera, a digital camcorder, or other type of video recorder that may be positioned adjacent to the monitor 10 so that images on the display 12 of the monitor 10 may be captured. The use of this camera 45 will be discussed in greater detail below with respect to FIG. 4.

Figure 3:
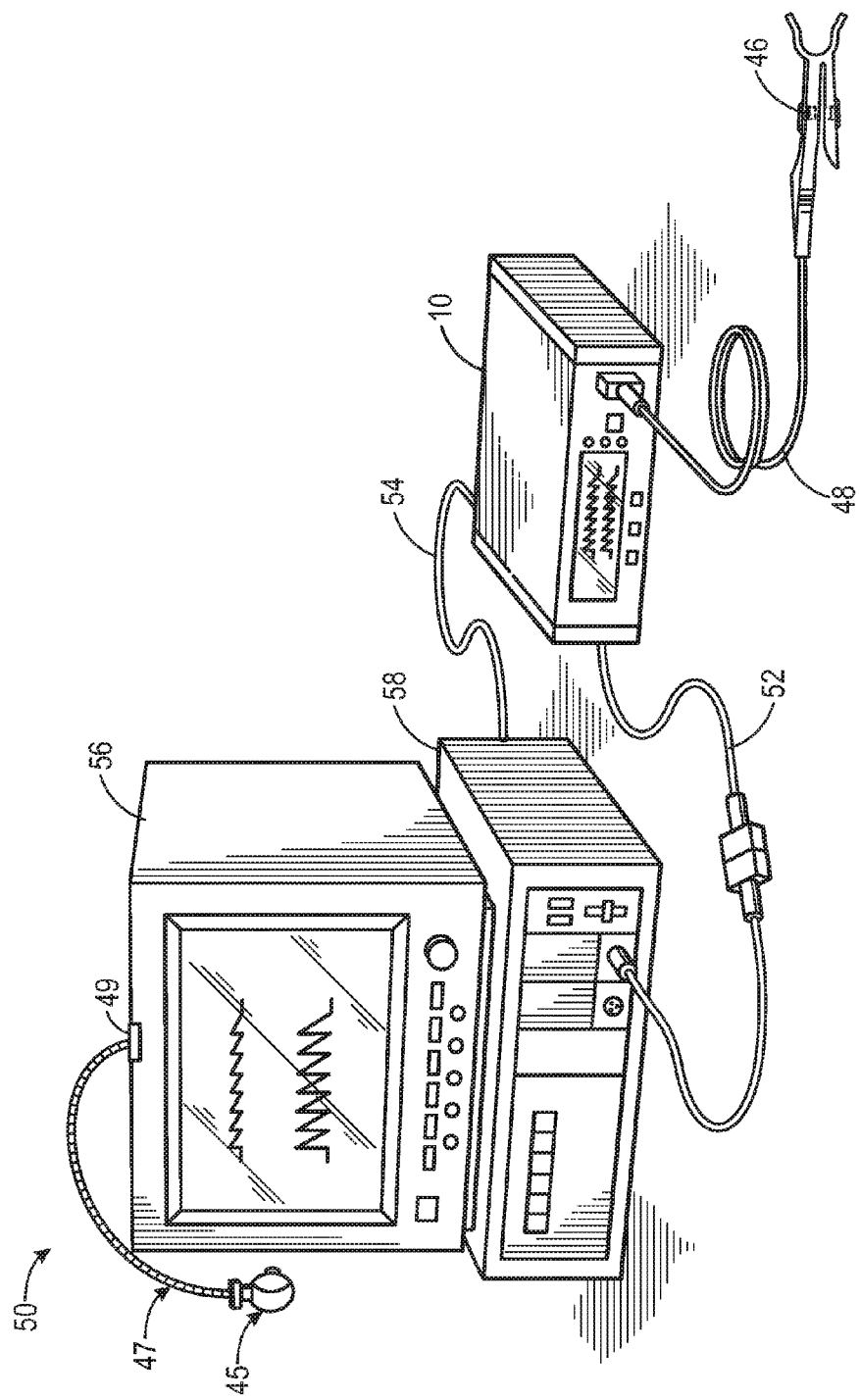
FIG. 3 illustrates a view of the patient monitor of FIG. 1 in conjunction with a multi-parameter patient monitor, in accordance with an embodiment.

As noted above, the monitor 10 may be used with a sensor 46, as illustrated in FIG. 3. It should be appreciated that a cable 48 of the sensor 46 may be coupled to the monitor 10 or it may be coupled to a transmission device (not shown) to facilitate wireless transmission between the sensor 46 and the monitor 10. The sensor 46 may be any suitable sensor 46, such as a DS100A sensor, a Max-Fast® sensor, or a Softcare® sensor available from Nellcor Puritan Bennett, LLC. Furthermore, to upgrade conventional pulse oximetry provided by the monitor 10 to provide additional functions, the monitor 10 may be coupled to a multi-parameter patient monitor 50 via a cable 52 connected to a sensor input port or via a cable 54 connected to a digital communication port. The multi-parameter patient monitor 50 may include both a display 56 and a base 58. The display 56 of the multi-parameter patient monitor 50 may operate to display a plethysmographic ("pleth") waveform display 16, an oxygen saturation display 18, a pulse rate display 20, and/or other information from one or more patient monitors 10. The base 58 may operate to receive data from one or more patient monitors 10 and transmit that data to the display 56. Additionally, another embodiment of the camera 45 is illustrated in FIG. 3. The camera 45 may be coupled to the display 56 via a support 47 (e.g., a flexible arm) and a fastener 49 (e.g., a bracket). In this manner, the camera 45 may be positioned to allow for capturing an image of a desired portion of the display 56.

Alternatively, monitor 10 illustrated in FIG. 3 may be implemented as part of the multi-parameter patient monitor 50. That is, components of the monitor 10 may be located, for example, in the base 58 of the multi-parameter patient monitor 50. In this configuration, cables 52 and 54 illustrated in FIG. 3 may be removed and cable 48 (as well as sensor 46 attached thereto) may be directly coupled to the base 58 of the multi-parameter patient monitor 50. Thus, in this configuration, the multi-parameter patient monitor 50 may operate to perform the functions of the monitor 10 directly.

Figure 4:
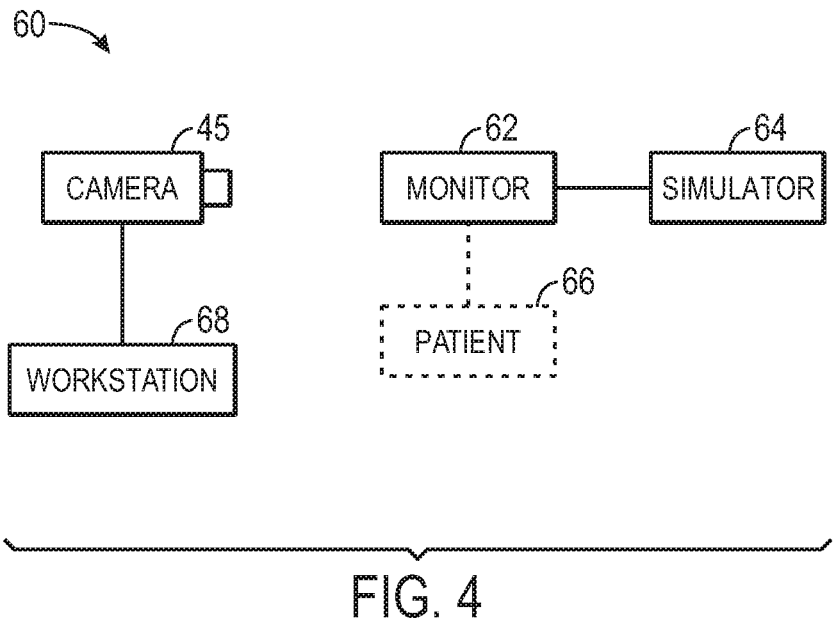
FIG. 4 illustrates a data capture system used in conjunction with the pulse oximeter in FIG. 1, in accordance with an embodiment.

FIG. 4 illustrates a block diagram including a system 60 that may be used in conjunction with the patient monitor 10 and/or the multi-parameter patient monitor 50 described above. FIG. 4 includes a monitor 62 that may represent either the patient monitor 10 and/or the multi-parameter patient monitor 50. FIG. 4 also includes a simulator 64 coupled to the monitor 62. Additionally, the system 60 may include a camera 45 and a workstation 68. The simulator 64 may be, for example, a portable and/or hand held device that may emulate signal that would be sent from a sensor 46 to the monitor 62. That is, the simulator 64 may simulate operational characteristics of a pulse oximetry sensor 46 (i.e., the simulator 64 may be a pulse oximetry sensor 46 simulator). One example of such a simulator 64 is an SRC-MAX Portable Oximetry Tester available from Nellcor Puritan Bennett, LLC.

Additionally, it should be noted that in place of the simulator 64 of FIG. 4, a patient 66 may be coupled to the monitor 62 via a sensor 46. That is, the sensor 46 would operate to measure physiological parameters of a patient 66 and transmit sensor signals to the monitor 62. Accordingly, whether a patient 66 is being actively monitored or whether a simulator 64 is being utilized to emulate signals that might otherwise be generated via patient 66 monitoring, the monitor 62 may generate, for example, a $SpO_2$ value, a SPDi index, and/or pulse rate based on received signals for display.

As the simulator 64 is performing one or more simulations on the monitor 62 (e.g., generating data values that correspond to a sensor signals for a range of physiological parameters of a patient), a camera 45 may be positioned such that the camera 45 may record the results of the simulations as they are displayed on the monitor 62. Additionally or alternatively, the camera 45 may be positioned such that the camera 45 may record the results of the monitoring of a patient as they are displayed on the monitor 62. In one embodiment, the camera 45 may be a free standing device such as a digital camera, a digital camcorder, or other type of video recorder. Thus, the camera 45 may include, for example, a lens, a digital sensor chip, and a memory, among other components. The lens may be utilized to focus light (i.e., an image to be captured by the camera 45) to the digital sensor chip, which transforms the focused light into digital information for storage in the memory of the camera 45. The digital sensor chip may be, for example, an image sensor such as a charge coupled device (CCD) or a complementary metal oxide semiconductor (CMOS). In one embodiment, the camera 45 may capture still images. Additionally, the camera 45 may capture video images. That is, when positioned adjacent to the monitor 62, as illustrated in FIG. 4, the camera 45 may be able to capture still images and/or video of any information displayed on the monitor 62, for example, as a simulation is occurring or as a patient 66 is being monitored.

The camera 45 may be a high resolution camera. For example, the camera may be a 6, 8, 10, 12 or more megapixel camera (i.e., such that the megapixel values for the camera are equivalent to the number of image sensor elements in the camera). Additionally, the camera 45 may be a high definition video recorder capable of recording images in 1080 p (i.e., such that the camera 45 is characterized by capturing and being able to output video with 1,080 lines of vertical resolution). Furthermore, it is envisioned that the camera 45 may also be incorporated into workstation 68. That is, the workstation 68 may include the camera 45 as a component in, for example, the housing of the workstation 68. Moreover, in one embodiment, the camera 45, the simulator 64, and one or more software programs (i.e., machine readable code loadable into a tangible computer readable storage such as a CD-ROM, a flash drive, or other tangible computer readable storage medium) including an image recognition program, an optical character recognition program, and/or other image capture and/or conversion programs may be grouped together as a kit for utilization together in capturing images from the monitor 62.

Figure 5:
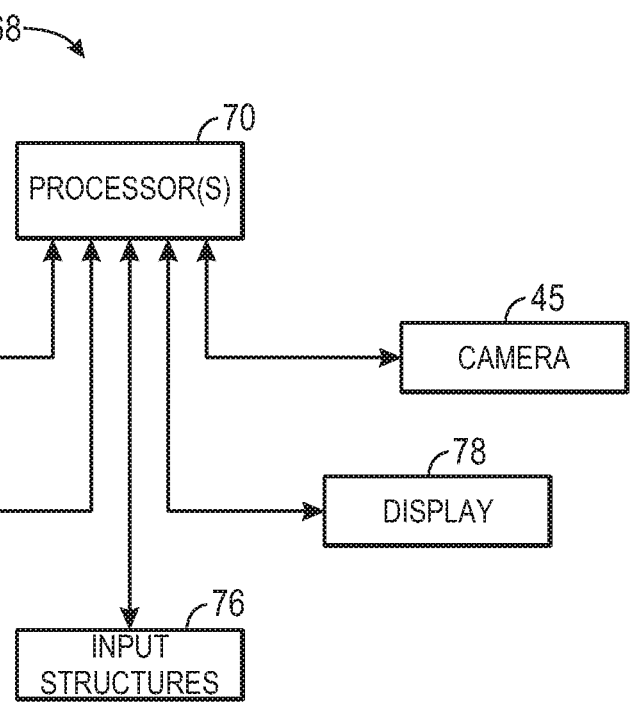
FIG. 5 illustrates a block diagram of data capture elements of the data capture system of FIG. 4, in accordance with an embodiment.

FIG. 5 illustrates an example of various internal components of the workstation 68. Those of ordinary skill in the art will appreciate that the various functional blocks shown in FIG. 5 may include hardware elements (including circuitry), software elements (including computer code stored on a machine-readable medium) or a combination of both hardware and software elements. In the presently illustrated embodiment of the workstation 68, the components may include one or more processors 70, a memory device 72, non-volatile storage 74, input structures 76, a display control 78, and a camera 45 (which, as noted above, may be internal to the workstation 68 or coupled to the workstation 68 via, for example, an input/output port such as a universal serial bus port).

With regard to each of these components, it is noted that the processor(s) 70 may provide the processing capability to execute an operating system, programs, user and application interfaces, and/or any other functions of the workstation 68. The processor(s) 70 may include one or more microprocessors, such as one or more "general-purpose" microprocessors, one or more special-purpose microprocessors and/or ASICS, or some combination of such processing components. Additionally, the processor(s) 70 may include one or more reduced instruction set (RISC) processors, as well as graphics processors, video processors, audio processors, and the like. As will be appreciated, the processor(s) 70 may be communicatively coupled to one or more data buses or chipsets for transferring data and instructions between various components of the workstation 68.

Programs or instructions executed by the processor(s) 70 may be stored in any suitable manufacture that includes one or more tangible, computer-readable media at least collectively storing the executed instructions or routines, such as, but not limited to, the memory devices and storage devices described below. Also, these programs encoded on such a computer program product may also include instructions that may be executed by the processor(s) 70 to enable the workstation 68 to provide various functionalities, including those described herein.

Instructions or data to be processed by the processor(s) 70 may be stored in a computer-readable medium, such as memory 72. The memory 72 may include a volatile memory, such as random access memory (RAM), and/or a non-volatile memory, such as read-only memory (ROM). The memory 72 may store a variety of information and may be used for various purposes. For example, the memory 72 may store firmware for the workstation 68 (such as basic input/output system (BIOS)), an operating system, and various other programs, applications, or routines that may be executed on the workstation 68. In addition, the memory 72 may be used for buffering or caching during operation of the workstation 68.

The components of workstation 68 may further include other forms of computer-readable media, such as non-volatile storage 74 for persistent storage of data and/or instructions. The non-volatile storage 74 may include, for example, flash memory, a hard drive, or any other optical, magnetic, and/or solid-state storage media. The non-volatile storage 74 may also be used to store firmware, data files, software programs, wireless connection information, and any other suitable data. Examples of programs that may be stored in the non-volatile storage 74 include image recognition programs, optical character recognition programs, or other image capture and/or conversion programs.

Additionally, input structures 76 may be present in the workstation 68. The input structures may include the various devices, circuitry, and pathways by which user input or feedback is provided to the processor(s) 70. Such input structures 76 may be configured to control a function of the workstation 68, applications running on the workstation 68, and/or any interfaces or devices connected to or used by the workstation 68. Non-limiting examples of the input structures 76 include buttons, sliders, switches, control pads, keys, knobs, scroll wheels, keyboards, mice, touchpads, and so forth. User interaction with the input structures 76, such as to interact with a user or application interface displayed on a display 78 (which may be used to display various images generated by the workstation 68), may generate electrical signals indicative of user input. These input signals may be routed via suitable pathways, such as an input hub or bus, to the processor(s) 70 for further processing. As will be discussed in greater detail below, the processor(s) 70 may operate in conjunction with the camera 45 to capture information displayed on the monitor 62.

Figure 6:
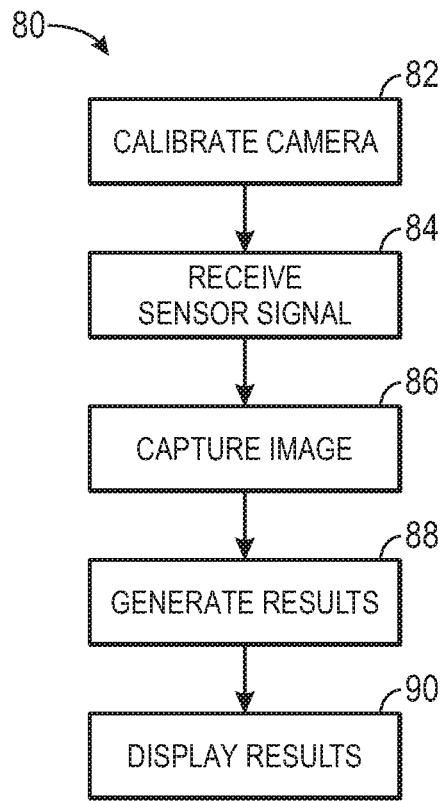
FIG. 6 illustrates a flow chart detailing the operation of the data capture system of FIG. 4, in accordance with an embodiment.

FIG. 6 illustrates a process 80 whereby monitor 62 information may be collected. In step 82, the camera 45 may be calibrated. This calibration process may include focusing the camera 45 on one or more portions of the monitor 62. For example, the processor 70 may transmit a signal to the camera 45 that causes the camera 45 to capture an image (i.e., take a picture). This image may be transmitted to the processor 70 where it may be processed via an optical character recognition program, which may be stored in storage 74 and run by the processor 70. The optical character recognition program may determine if the captured image is properly focused. That is, the optical character recognition program may compare the image to known optical characters and determine if the image includes one or more of the known optical characters. If known optical characters are matched during this comparison, the process may proceed to step 84. If however, known optical characters are not matched during this comparison, then the processor 70 may transmit a signal to the camera 45 that causes the camera 45 to adjust a focus position of the lens of the camera. Subsequently the processor 70 may transmit a signal to the camera 45 that causes the camera 45 to capture an image (i.e., take a picture). This new image may be processed via the optical character recognition program in the manner described above. This process may also be repeated until known optical characters are matched during the optical character recognition program comparison. In another embodiment, a user may manually adjust the focus position of the camera during the calibration step 82.

Additionally, calibration of the camera 45 in step 82 may include adjusting the camera 45 to capture images based on the refresh rates of the monitor 62, based on the type of monitor 62 utilized (e.g., a light emitting diode display or a liquid crystal display), and/or based on the location of data to be captured from the monitor 62 (e.g., the location of $SpO_2$, SPDi, and/or pulse rate data on the monitor 62).

In step 84, a sensor signal is received by the monitor 62. This sensor signal may be received from a sensor 46 that is coupled to a patient 66. Alternatively, the sensor signal received by the monitor 62 may be generated by the simulator 64. That is, the simulator 64 may initiate a simulation may emulate sensor signals that would be generated in response to various conditions occurring while a patient 66 is being monitored. For example, the simulator 64 may transmit sensor signals to the monitor 62 that correspond to oxygen saturation levels, saturation pattern detection index levels, and/or a pulse rates that might occur if the monitor 62 were in use to monitor physiological parameters of a patient 66. In one embodiment, this simulation may include transmission of a series of signals from the simulator 64 that, taken together, correspond to a range of predetermined values that the monitor 62 might typically receive during operation. That is, the simulator 64 may transmit signals that are to generate an alarm in the monitor 62 as indicating, for example, oxygen saturation levels, saturation pattern detection index levels, and/or a pulse rates that are too low (e.g., below a lower threshold value), followed by transmission of signals that fall in a typically normal range (e.g., between a lower threshold value and an upper threshold value) to the monitor 62. Subsequently, the simulator 64 may transmit signals that are to generate an alarm in the monitor 62 indicating, for example, oxygen saturation levels, saturation pattern detection index levels, and/or a pulse rates that are too high (e.g., above an upper threshold value).

Furthermore, the simulator 64 may repeat this operation of transmitting signals to the monitor 62 to simulate more than one physiological characteristic. For example, the simulator 64 may transmit a series of signals that cause the monitor 62 to generate displayed results corresponding to oxygen saturation levels followed by the simulator 64 transmitting a series of signals to the monitor 62 to cause the monitor 62 to generate displayed results corresponding to pulse rates. Thus, by transmitting data signals that correspond to ranges of parameters for more than one physiological characteristic, the monitor 62 may be tested to insure its proper operation with respect to multiple functions.

In another embodiment, the simulation initiated by the simulator 64 may include generation of structured errors that may occur during operation of the monitor 62. For example, the simulator 64 may generate a series signals each designed to mimic a physiological response in a patient 66 that would generate an error in the monitor 62 and/or to mimic a condition (such as sensor 46 having been misapplied) that would generate an error in the monitor 62. That is, signals that would elicit normal (i.e., non-error) responses in the monitor 62 may be omitted from transmission to the monitor 62 by the simulator 64 during a structured error simulation.

As the simulator 64 is performing one or more simulations on the monitor 62 or as actual values are being transmitted by the sensor 46, the camera 45 may capture one or more images in step 86. The capturing of these images in step 86 may correspond to the camera 45 taking a picture as the results of the one or more simulations initiated in step 84 are displayed on the monitor 62. That is, the capturing of one or more images in step 86 may be accomplished by a user activating a button or other input device on the camera 45 to capture a still image. Alternatively, the capture of one or more images in step 86 may be accomplished by the processor 70 issuing a capture signal to the camera 45 that causes the camera 45 to capture a still image in a manner similar to if a user activated a button or other input device on the camera 45.

Additionally, it should be noted that step 86 may include, for example, multiple capture signals being transmitted from the processor 70 to the camera 45 across a predefined time period. For example, the processor 70 may transmit a series of capture signals to the camera 45 such that each time a data signal is transmitted to the monitor 62 from the simulator to generate a response on the display 12 of the monitor 62, a still image corresponding to the displayed result is captured by the camera 45, as directed by a respective capture signal received at the camera 45 from the processor 70. That is, the processor 70 may transmit capture signals to the camera 45 such that the capture signals correspond to the number results displayed on the display 12 of the monitor 62 during one or more simulations or during the course of monitoring a patient 66.

Alternatively, step 86 may include a video capture of the response of the monitor 62 to a simulation or to monitoring of a patient 66. For example, the processor 70 may transmit a video activation signal to the camera 45, which may cause the camera 45 to capture moving images in the form of video instead of still images. The processor 70 may subsequently transmit a video capture signal to the camera 45 that causes the camera 45 to begin to capture video of the display 12 of the monitor 62. In this manner, a video log of the results of the sensor signals received in step 84 may be recorded. Additionally, the camera 45 may continuously process video images, capture certain changes that are displayed on the monitor 62 as still images, and, for example, time stamp the captured still images (i.e., add time and or data information to the captured still image).

In one embodiment, the video activation signal may be transmitted by the processor 70 in conjunction with step 84 (i.e., the recording of the results of the simulation may be coordinated with the time that the simulation is run or with a period of time that a patient 66 is monitored). Additionally, the processor 70 may transmit a video deactivation signal to the camera 45 to end the recording of the results. This video deactivation signal may be transmitted, for example, in conjunction with the termination of the simulation being run on the monitor 62 or at a time chosen to cease monitoring of the patient 66.

The results of the image capture in step 86 may be generated in step 88. Generation of the results of the simulation in step 88 may include, for example, conversion of the captured images in step 86 into readily displayable data. For example, generation of results in step 88 may include conversion of optical characters or other images into American Standard Code for Information Interchange (ASCII) printable characters (i.e., alphanumeric characters). This conversion may be accomplished through the use of the optical character recognition program discussed above, which may be stored in storage 74 and run by the processor 70. The optical character recognition program may compare the captured image with known optical characters to determine if the captured image includes one or more of the known optical characters. If known optical characters are matched during this comparison, the optical character recognition program may store the result of the comparison as a result value, for display, for example, as an ASCII character in step 90. If no match is made during the comparison, the image, for example, may be blurred or refocused by the optical character recognition program and then a comparison may be reattempted.

Thus, through the comparison operation described above, the optical character recognition program may store results of a simulation of the monitor 62 or results of the monitoring of a patient 66, as captured by the camera 45. Moreover, the processor 70 may transmit the results generated in step 88 to a display 78 in step 90, so that the results may be reviewed by a user. In one embodiment, the display of results in step 90 may be accomplished via a user actively requesting the results to be displayed. That is, a user may initiate a program that directs the processor 70 to display the results of the optical character recognition program conversion of the captured images on the display 78.

Additionally or alternatively, a user may actively request that any video captured by the camera 45 be displayed on the display 78 in step 90. That is, a user may initiate a program that directs the processor 70 to display video of the monitor 62 collected by the camera 45 on the display 78. In this manner, a user may review the results of a simulation run on the monitor 62 to, for example, insure that the monitor 62 responds in an anticipated manner (i.e., functions correctly) with respect to various situations (i.e., inputs) that may occur during operation of the monitor 62 That is, the monitor 62 may be tested so that proper operation of the monitor 62 may be verified. Similarly, results from the monitoring of a patient 66 may be logged for further analysis.

Figure 7:
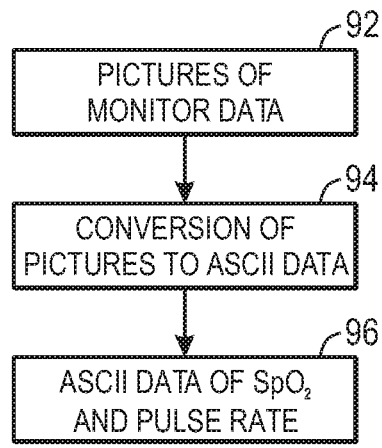
FIG. 7 illustrates a flow chart detailing a specific example of the operation of the data capture system of FIG. 4, in accordance with an embodiment.

FIG. 7 illustrates a particular embodiment of the operation of the data capture by camera 45 from monitor 62. In step 92, pictures of monitor data are captured by the camera 45 from the monitor 62. As noted above, this monitor data may be generated as a result of a simulation being run on the monitor 62 or may be generated in response to physiological parameters of a patient 66 being measured by a sensor 46.

The pictures captured in step 92 may be converted in step 94 into ASCII data. This conversion may be accomplished through the use of the optical character recognition program discussed above, which may be stored in storage 74 and run by the processor 70. Through, for example, the comparison operation performed by the optical character recognition program, ASCII data relating to both $SpO_2$ and pulse rate values that were displayed on the monitor 62 are generated, as shown in step 96. As detailed above, this $SpO_2$ and pulse rate ASCII data may be analyzed to determine the proper operation of the monitor 62 or the $SpO_2$ and pulse rate ASCII data may be analyzed to determine the results of patient monitoring, depending on the source of the data displayed by the monitor 62.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A system comprising:
   a monitor adapted to:
      receive a first simulated pulse oximetry input signal and a subsequent second simulated pulse oximetry input signal from a simulator;
      generate a first result and a subsequent second result based on the first simulated pulse oximetry input signal and the second simulated pulse oximetry input signal, respectively; and
      display the first result as a first image and, subsequently, the second result as a second image;
   a camera adapted to capture the first image and to subsequently capture the second image of the display; and
   a workstation adapted to receive the first image and the second image of the display from the camera, wherein the workstation is adapted to convert the first image and the second image of the display into displayable data, and wherein the workstation is configured to transmit a first activation signal and a subsequent second activation signal to the camera based at least in part upon the first simulated pulse oximetry input signal and the second simulated pulse oximetry input signal, respectively, to coordinate the capture of the first image and the second image, respectively.

2. The system of claim 1, wherein the workstation is adapted to identify at least one portion of each of the first image and the second image as including an alphanumeric character and generate a corresponding result character based on the respective alphanumeric character as the displayable data.

3. The system of claim 1, wherein the workstation comprises a workstation display, wherein the workstation is adapted to display the displayable data on the workstation display.

4. The system of claim 1, wherein the simulator comprises a pulse oximetry sensor simulator adapted to generate the first simulated pulse oximetry input signal and the second simulated pulse oximetry input signal and transmit the first input simulated pulse oximetry signal and the second simulated pulse oximetry input signal to the monitor.

5. The system of claim 1, wherein the monitor comprises a pulse oximetry monitor.

6. A kit, comprising:
   a simulator adapted to generate a first simulated pulse oximetry signal and a subsequent second simulated pulse oximetry signal;
   a camera adapted to capture a first image and to subsequently capture a second image generated on a first display in response to the first simulated pulse oximetry signal and the second simulated pulse oximetry signal, respectively; and
   machine readable code loadable into a non-transitory tangible computer readable storage, wherein the machine readable code operates to direct a processor to transmit a first activation signal and a subsequent second activation signal to the camera based on the first simulated pulse oximetry signal and the second simulated pulse oximetry signal, respectively, to coordinate the capture of the first image and the second image, respectively, and wherein the machine readable code operates to direct the processor to convert at least a portion of the first image and the second image into result data for display on a second display.

7. The kit of claim 6, wherein the machine readable code operates to direct the camera to focus on a particular portion of the first display.

8. The kit of claim 6, wherein the machine readable code operates to direct the processor to identify at least one portion of each of the first image and the second image as including an alphanumeric character and generate a corresponding result character as the result data.

9. The kit of claim 6, wherein the machine readable code operates to direct the camera to capture a still image.

10. The kit of claim 6, the machine readable code operates to direct the camera to capture a video image.

11. A method comprising:
    generating in a simulator a first simulated pulse oximetry signal and a subsequent second simulated pulse oximetry signal;
    transmitting, via the simulator, the first simulated pulse oximetry signal and subsequently transmitting, via the simulator, the second simulated pulse oximetry signal to a pulse oximetry monitor;
    generating in the pulse oximetry monitor a first result and a subsequent second result based at least in part upon the first simulated pulse oximetry signal and the second simulated pulse oximetry signal, respectively;
    displaying the first result as a first image and, subsequently, the second result as a second image on a display of the pulse oximetry monitor;
    transmitting, via a processor, a first activation signal and a subsequent second activation signal to a camera based at least in part upon the first and the second simulated pulse oximetry signal, respectively; and
    capturing, via the camera, the first image and, subsequently, the second image of the display in response to the first activation signal and the second activation signal, respectively.

12. The method of claim 11, comprising calibrating the camera by focusing the camera on one or more portions of the display, capturing a third image, and determining if an optical character is present in the third image.

13. The method of claim 11, wherein the first result is indicative of at least one of a pulse rate, a saturation pattern detection index, or an oxygen saturation level based on the signal, and wherein the first image comprises an indication of at least one of the pulse rate, the saturation pattern detection index, or the oxygen saturation level.

14. The method of claim 13, wherein capturing the first image comprises capturing a still image of at least one of the pulse rate, the saturation pattern detection index, or the oxygen saturation level on the display of the pulse oximetry monitor.

15. The method of claim 13, wherein capturing the first image comprises capturing a video image of at least one of the pulse rate, the saturation pattern detection index, or the oxygen saturation level on the display of the pulse oximetry monitor.

16. The method of claim 11, comprising converting the first image and the second into result data.

17. The method of claim 16, wherein converting the first image and the second image comprises identifying at least one portion of each of the first image and the second image as including an alphanumeric character and generating a corresponding result character based on the alphanumeric character as the result data.

18. The method of claim 16, comprising displaying the result data on a second display.

19. The system of claim 1 wherein the first simulated pulse oximetry input signal comprises an error signal, and wherein the first result comprises an error indication.

20. The system of claim 1, wherein the workstation is adapted to calibrate the camera by focusing the camera on one or more portions of the display, capturing a third image, determining if an optical character is present in the third image, and adjusting a focus of the camera in response to determining that an optical character is not present in the third image.

* * * * *